United States Patent [19]

Maruyama

[11] Patent Number: 5,278,630
[45] Date of Patent: Jan. 11, 1994

[54] ABSORBANCE DETECTOR

[75] Inventor: Shuzou Maruyama, Kyoto, Japan

[73] Assignee: Shimadzu Corporation 1, Kyoto, Japan

[21] Appl. No.: 751,799

[22] Filed: Aug. 29, 1991

[30] Foreign Application Priority Data

Aug. 29, 1990 [JP] Japan ................................. 2-228646

[51] Int. Cl.⁵ .............................................. G01J 3/28
[52] U.S. Cl. ..................................... 356/328; 356/334
[58] Field of Search ................................. 356/328, 334

[56] References Cited

U.S. PATENT DOCUMENTS 4,565,447 1/1986 Nelson ................................. 356/319

Primary Examiner—Richard A. Rosenberger
Assistant Examiner—K. P. Hantis
Attorney, Agent, or Firm—Thomas R. Morrison

[57] ABSTRACT

An absorbance detector measures absorbance alternately at first and second wavelengths. When a measurement is made at one wavelength, a projection is made, based on past measurement, of the value of absorbance at the other wavelength. A ratio is taken of the measured value at one wavelength with the projected absorbance at the other wavelength. Linear and non-linear projections are disclosed.

6 Claims, 3 Drawing Sheets

ABSORBANCE DETECTOR

BACKGROUND OF THE INVENTION

The present invention relates to absorbance detectors for high-performance liquid chromatography and, more particularly, to an absorbance detector for analyzing qualitatively a peak purity of a chromatogram by scanning two wavelengths alternately to calculate a ratio of absorption constants measured at these two wavelengths.

An absorbance detector using a spectroscope scanning at two wavelengths is well known. This type of detector drives a spectroscope scan at two wavelengths $\lambda_1$ and $\lambda_2$ to measure absorption constants at these wavelengths. In one prior-art technique, the absorption constant newly measured at one wavelength is combined with the most recently measured absorption constant at the other wavelength to form a ratio. With data measured alternately at wavelength $\lambda_1$ at times $(n-2)$ and $(n)$ and at wavelength $\lambda_2$ at times $(n-1)$ and $(n)$, two succeeding chromatograph ratios $A\lambda_1(n-2)/A\lambda_2(n-1)$, $A\lambda_1(n)/A\lambda_2(n+1)$ are formed. It will be noted that the calculated chromatography ratios use absorption constants measured at different points in time. That is, the first chromatograph ratio above uses absorption data taken at wavelength $\lambda_1$ at time $(n-2)$ while the absorption data taken at wavelength $\lambda_2$ is taken at time $(n-1)$, one time period removed. The second chromatograph ratio similarly uses data taken at times that are offset by one time unit. The lack of simultaneity in the measurements at the two wavelengths produces an error when the concentration of material being measured is changing. This follows from the fact that a chromatography ratio, for a single component, is constant if it is calculated for a single peak. However, if the data forming the ratio of absorption constants are not taken simultaneously, the chromotography ratio is not constant, even when measuring a single component, and therefore it is not possible to measure peak purity accurately.

Another absorbance detector of the prior art uses the ratio of moving averages of absorption constants measured at wavelengths $\lambda_1$ and $\lambda_2$. The chromatography ratio using a moving average is given by:

$$(A\lambda_1(n-2)+A\lambda_1(n)+\ldots)/(A\lambda_2(n-1)+A\lambda_2(n+1)+\ldots).$$

Calculating a moving average uses the ratio of past data. This causes a time delay in determining the peak purity and therefore is not preferably in a minute-to-minute measurement system.

OBJECTS AND SUMMARY OF THE INVENTION

Accordingly, it is an object of the invention to provide an absorbance detector that overcomes the problems of the prior art.

It is a further object of the invention to provide an absorbance detector that is capable of detecting a peak concentration in real time in a flow of a substance being measured.

It is a further object of the invention to provide an absorbance detector that detects a correct peak concentration by calculating a present or future absorption constant at each of two different wavelengths $\lambda_1$ and $\lambda_2$ and using the two calculated values to form a ratio. This provides minute-to-minute measurement by eliminating time delay in the data used to calculate a chromatography ratio.

Briefly stated, the present invention provides an absorbance detector that measures absorbance alternately at first and second wavelengths. When a measurement is made at one wavelength, a projection is made, based on past measurement, of the value of absorbance at the other wavelength. A ratio is taken of the measured value at one wavelength with the projected absorbance at the other wavelength. Linear and non-linear projections are disclosed.

According to an embodiment of the invention, there is provided an absorbance detector comprising: means for alternately measuring absorbance of a material at first and second wavelengths to produce first and second absorbance values, respectively, means, effective during measurement of the first absorbance value, for predicting a value of the second absorbance value to produce a predicted second absorbance value, and means for taking a ratio of the first absorbance value and the predicted second absorbance value.

According to a feature of the invention, there is provided an absorbance detector comprising: a light source, a flow cell, a diffraction means between the light source and the flow cell, means for controlling the diffraction means to pass first and second wavelengths from a light source therethrough and into the flow cell, means for detecting the first and second wavelengths passing through the flow cell, first means, responsive to the means for detecting, for determining a first absorption constant at the first wavelength, second means, responsive to the means for detecting, for determining a second absorption constant at the second wavelength, means for forming a ratio the first absorption constant and the second absorption constant, and the means for forming a ratio including means for projecting a plurality of past measurements of the first absorption constant to predict a value of the first absorption constant at a time of measurement of the second absorption constant, the means for forming a ratio employing a current absorption measurement with a predicted absorption value, whereby the ratio employs substantially current data.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
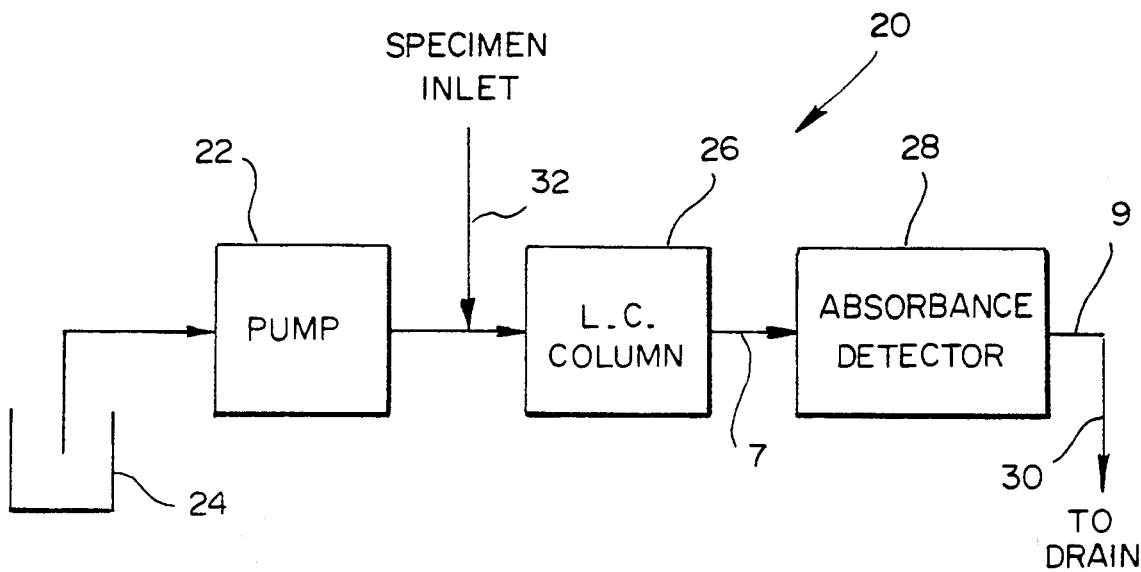
FIG. 1 is a simplified block diagram of a chromatograph system employing an absorbance detector according to an embodiment of the invention.

Referring to FIG. 1, a liquid chromatograph system 20 includes a pump 22 to pump a carrier liquid from a container 24 through a liquid chromatograph column 26 and an absorbance detector 28 to a drain line 30. A specimen injection port 32 permits the injection of a specimen to be analyzed into liquid chromatograph column 26. The specimen is a liquid which includes one or more chemical components to be separated and analyzed.

The different chemical components pass through liquid chromatograph column 26 at different rates. If a mixture of components passes through liquid chromatograph column 26, they elute at different times characteristic of the individual components. Thus, by measuring the retention times at which the peak concentrations of materials elute from liquid chromatograph column 26, knowledge can be gained of the materials in the mixture. In addition, knowing the material exiting liquid chromaograph column 26 at any given time, a measurement of optical absorbance at that time can be interpreted in terms of the concentration of the material.

As discussed in the background section above, there is a problem in determining the exact time or times at which the peak or peaks of absorbance takes place.

Figure 2:
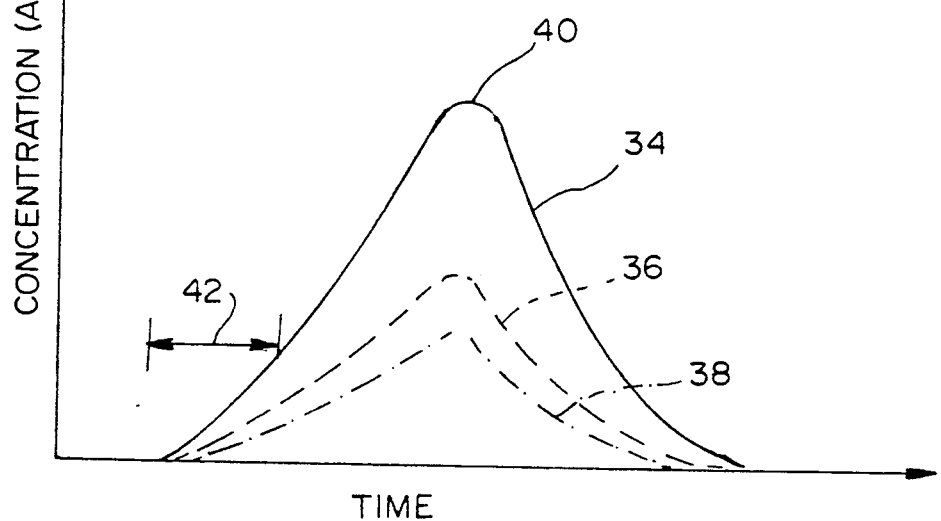
FIG. 2 is a set of curves illustrating the concentration of a substance with respect to time, and absorbance curves related to the concentration.

Referring to FIG. 2, a solid-line concentration curve 34 represents the concentration over time of a single component exiting liquid chromatograph column 26 and entering absorbance detector 28. A dashed $\lambda_1$ curve 36 represents the output of absorbance detector 28 in response to optical transmission measurements at the wavelength $\lambda_1$. A dot-dash $\lambda_2$ curve 38 represents the output of absorbance detector 28 in response to optical transmission measurements at wavelength $\lambda_2$.

In order to accurately determine the type of material being analyzed, and to determine its concentration, it is necessary to detect the exact time at which a peak concentration 40 exists in the material passing through absorbance detector 28. It is in the task of determining the exact time of peak concentration 40 that prior-art systems have a problem, and to which the present invention is directed.

Figure 3:
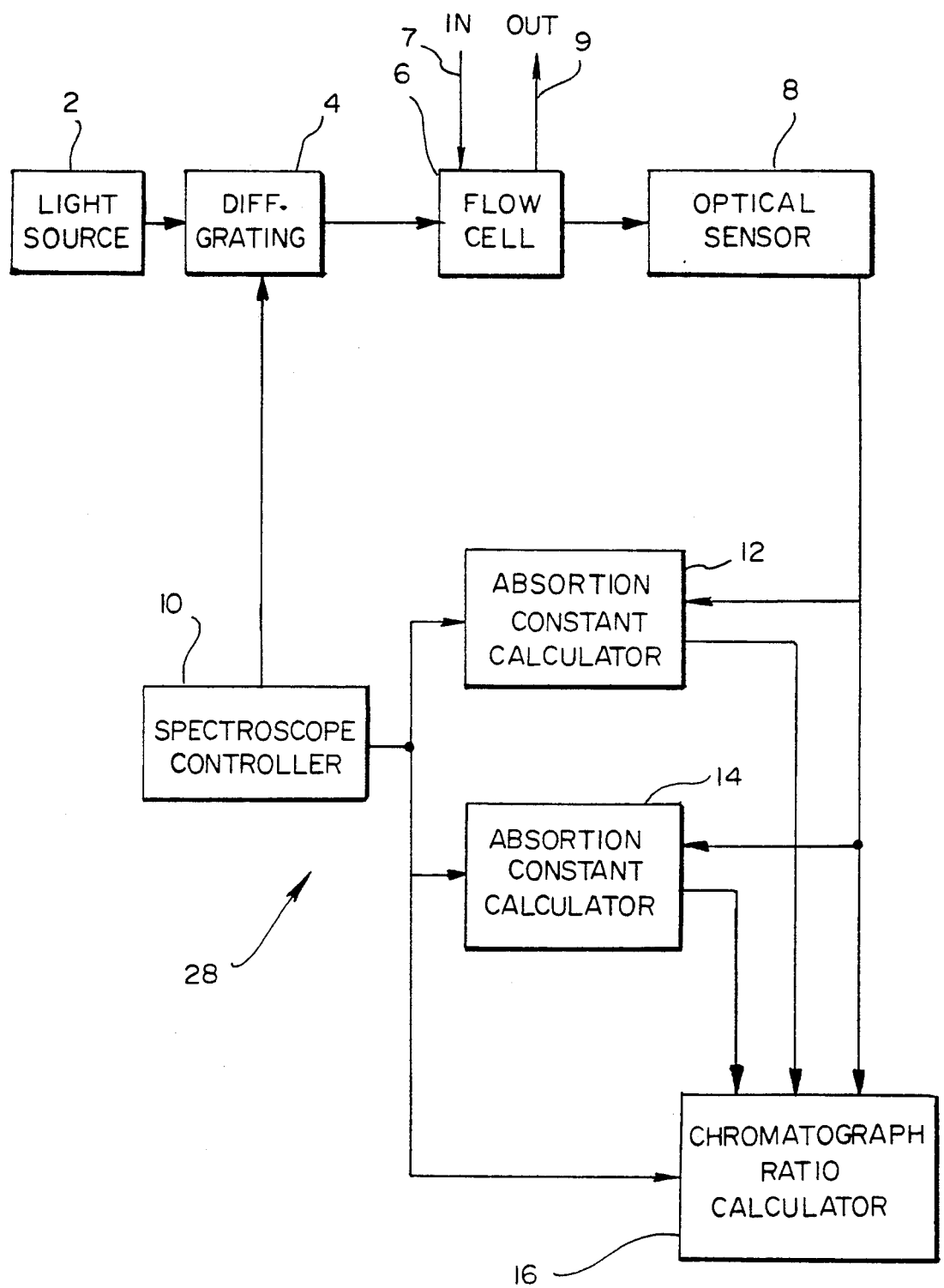
FIG. 3 is a block diagram of an absorbance detector of FIG. 1.

Referring now to FIG. 3, absorbance detector 28 includes a light source 2 directing a beam of light to a spectroscope 4. Spectroscope 4 may be of any suitable type including, for example, a diffraction grating. A spectroscope controller 10 oscillates the angle of diffraction grating 4 between two angles capable of permitting two narrow wavelength bands of light, $\lambda_1$ and $\lambda_2$ to pass therethrough and to enter a flow cell 6. An inlet tube 7 permits the entry into flow cell 6 of the material to be analyzed. A discharge tube 9 permits the material to pass out of flow cell 6. Flow cell 6 conventionally consists of a passage having transparent sides for permitting light from diffraction grating 4 to pass therethrough to impinge on an optical sensor 8 such as, for example, a photomultiplier, at the opposite side thereof. As the concentration of the substance to be measured increases, the amount of light reaching optical sensor 8 decreases. The absorbance (the amount by which the light is blocked by the substance) is calculated from the reduction in light received by optical sensor 8.

Light source 2 may be of any convenient type capable of emitting sufficient light at wavelengths $\lambda_1$ and $\lambda_2$. Although two-color light-emitting diodes or laser sources may be used, for convenience and cost it is preferred to use an incandescent light source consisting of, for example, a tungsten lamp, or a deuterium lamp. An incandescent light source provides a convenient continuous band of wavelengths from which spectroscope 4 can select the desired wavelengths. The exact wavelengths selected depend on the material being measured. Different materials whose absorbance is to be measured may be preferentially absorptive at different optical wavelengths. In practice, we have found that wavelength bands of from about 190 to about 370 nanometers (near ultra-violet) provide a band of wavelengths from which two suitable wavelengths can be selected by diffraction grating 4 at which many materials of interest have significant absorbance. Another wavelength band of from about 370 to 600 nanometers (visible light) is also suitable for many materials to be measured.

In a practical machine, we have found that it is desirable to leave the selection of wavelengths $\lambda_1$ and $\lambda_2$ at the option of the user, in order to broaden the adaptability of the apparatus. We have found that those skilled in the art are fully familiar with the requirements for selecting wavelengths for absorbance measurement. Accordingly, it is considered that a fuller description thereof is unnecessary.

The output of optical sensor 8 is applied to inputs of first and second absorption constant calculators 12 and 14. Outputs of first and second absorption constant calculators 12 and 14 are connected to a chromatograph ratio calculator 16. An output of spectroscope controller 10 is applied to first and second absorption constant calculators 12 and 14, and to chromatograph ratio controller 16.

In operation, when spectrscope controller 10 controls diffraction grating 4 to permit wavelength $\lambda_1$ to pass through flow cell 6 and its absorbance to be measured by optical sensor 8, it also enables first absorption constant calculator 12 to calculate the absorbance constant at this wavelength. The result of this calculation of first absorption constant calculator 12 is identified in chromatograph ratio calculator 16 with wavelength $\lambda_1$. Similarly, when spectroscope controller 10 controls diffraction grating 4 to permit wavelength $\lambda_2$ to pass through flow cell 6 and its absorbance to be measured by optical sensor 8, it also enables second absorption calculator 14 to calculate the absorbance constant at this wavelength. The result of this calculation of second absorption constant calculator 14 is identified in chromatograph ratio calculator 16 with wavelength $\lambda_2$.

$\lambda_1$ curve 36 and $\lambda_2$ curve 38 show the results of these calculations plotted over time as the concentration of the material being measured rises from near zero, passes peak concentration 40, and then declines to near zero.

Chromatograph ratio calculator 16 forms a ratio from which the time of peak concentration 40 can be determined.

Figure 4:
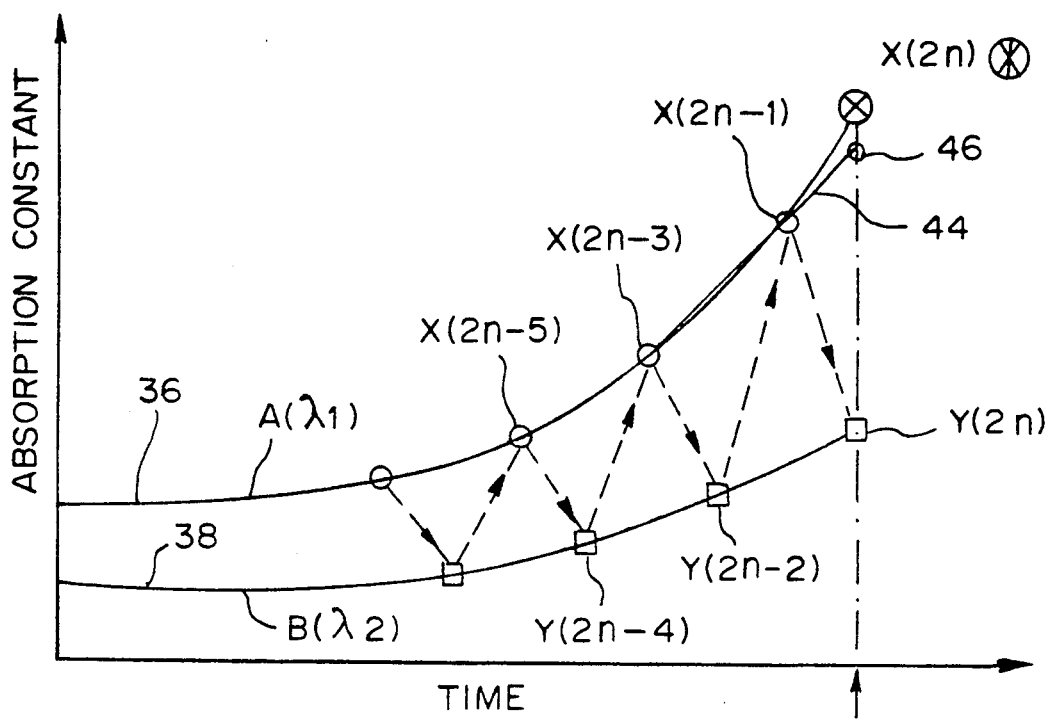
FIG. 4 is a set of curves to which reference will be made in describing the invention.

Referring now to FIG. 4, the problem of non-simultaneous acquisition of data is illustrated. For this purpose, it is assumed that a time interval in the product-flow curve identified by an interval 42 in FIG. 2 is being measured. The shape of the $\lambda_1$ absorbance curve $A\lambda_1$ is determined by discrete measurements taken at times $(2n-5)$, $(2n-3)$ and $(2n-1)$. Between the above measurements, the shape of the $\lambda_2$ absorbance curve $B\lambda_2$ is determined from discrete measurements taken at times $(2n-4)$, $(2n-2)$ and $(2n)$. Suppose it is desired to calculate the chromatograph ratio at time $2n$. A fresh measurement $Y(2n)$ is available for the amplitude of $B\lambda_2$, but the latest measurement $X(2n-1)$ is old by 1 time interval. This time skew in measurements would degrade seriously the accuracy by which the calculated chromatograph ratio can determine the peak of the concentration curve, and thereby degrade the accuracy of the entire apparatus.

Instead of relying on old data taken at time $(2n-1)$ for the amplitude of $\lambda_1$ curve 36 to calculate the chromatograph ratio at time $(2n)$, the present invention projects the value of curve 36, based on two or more past measurements, to predict the amplitude of $\lambda_1$ curve 36 at time $(2n)$. It then uses the predicted amplitude of curve $\lambda_1$ 36 at time $(2n)$, together with the currently measured amplitude of $\lambda_2$ curve 38, to calculate the chromatograph ratio.

Stepping backward one time period, at the time $(2n-1)$ when a fresh measurement of $A\lambda_1$ is available, two or more prior measured values of $B\lambda_2$ are employed to project the value of $B\lambda_2$ at time $(2n-1)$.

The prediction or projection discussed above may use any suitable algorithm. For example, linear projection may be employed using the two immediately prior values to project the prior measurements to the present time. This is illustrated in FIG. 4 by a line drawn through the points $X(2n-3)$ and $X(2n-1)$ which intersects a vertical line at time $(2n)$ at a point 46. Thus, the calculation of the absorbance ratio at time $(2n)$ employs the projected value at point 46, together with the currently measured value at $Y(2n)$.

It will be noted that the projected value at point 46 does not coincide with the actual value of $\lambda_1$ curve 36 at time $(2n)$. This prediction error may be reduced using a non-linear projection without departing from the spirit and scope of the invention. To develop a non-linear projection, the amplitudes of the three prior measurements of the $\lambda_1$ curve 36, at times $(2n-1)$, $(2n-3)$ and $(2n-5)$, may be employed to determine a fit between these points and a hypothetical curve. Then the hypothetical curve may be used for projecting the value of $\lambda_1$ curve 36 to time $(2n)$. Any suitable hypothetical curve may be used for this projection including, for example, a parabolic or exponential curve.

Another way to predict the absorption constant of $\lambda_1$ curve 36 at time $(2n)$ uses the equation $$X(2n)^* = X(2n-1) + X1(2n-1)/2 + X2(2n-1)/2$$

where $X(2n)^*$ is a predicted value of absorption constant for wavelength $\lambda_1$ when absorption constant is measured by wavelength $\lambda_2$ and $$X1(m) = X(m) - X(m-2)$$

$$X2(m) = X1(m) - X1(m-2).$$

When the absorption constant is measured on $\lambda_1$ curve 36, the absorption constant on $\lambda_2$ curve 38, corresponding to the time of measurement, may be projected using the same technique.

According to the description above when an absorption measurement is performed using wavelength $\lambda_1$, the absorption constant for $\lambda_1$ is a measured value at that point in time, denoted by $A\lambda_1$. The absorption constant for $\lambda_2$ is a value predicted from past measurements for that same point in time, denoted by $A\lambda_2^*$. The resulting chromatograph ratio is given by $A\lambda_1/A\lambda_2^*$. Similarly, when a measurement is performed at wavelength $\lambda_2$, the chromatograph ratio is given by $A\lambda_1^*/A\lambda_2$ where $A\lambda_1^*$ is a predicted value for $A\lambda_1$ and $A\lambda_2$ is a measured value at wavelength $\lambda_2$.

Figure 5:
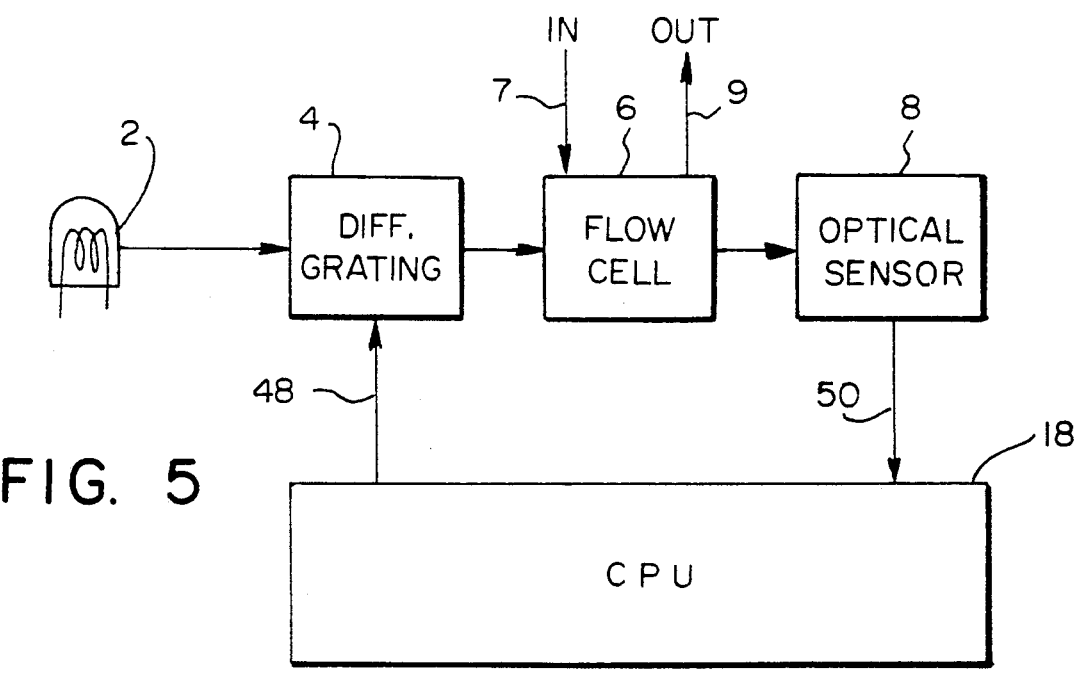
FIG. 5 is a block diagram of an absorbance detector according to a further embodiment of the invention.

Referring now to FIG. 5, a further embodiment of the invention employs a heavy hydrogen lamp that can be used as light source 2. Diffraction grating 4, flow cell 6 and optical sensor 8 are as described in connection with FIG. 3. The functions performed in the embodiment of FIG. 3 by spectroscope controller 10, first and second absorption constant calculators 12 and 14, and chromatograph ratio calculator 16 are all performed in the embodiment of FIG. 5 by a CPU 18. That is, a control signal on a line 48, from CPU 18 to diffraction grating 4, controls diffraction grating 4 to pass wavelengths $\lambda_1$ and $\lambda_2$ alternately to flow cell 6. The output of optical sensor 8 is connected on a line 50 to CPU 18. CPU 18 then performs the synchronizing and calculating functions as previously described.

One skilled in the art will recognize that the output of optical sensor 8 is an analog value, whereas CPU 18 operates on digital values. The presence of an analog-to-digital converter (not shown) is assumed in one of the illustrated elements, but is not shown in order to reduce clutter in the drawing.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An absorbance detector, comprising:
   a spectroscopic controller including
   means for alternately measuring absorbance of a flowing substance at first and second wavelengths to produce first and second measured absorbance values, at first and second times, respectively, and
   means for predicting, based on said second measured absorbance value, a predicted value of said second absorbance value, at said first time; and
   a chromatographic ratio calculator for determining a signal that represents a ratio between said first absorption signal and said second absorption signal, wherein said chromatographic ratio calculator includes;
   means for projecting a plurality of signals representing a plurality of past values of said first absorption signal to predict a value of said first absorption signal at a time of measurement of said second absorption signal, said chromatographic ratio calculator employing a current absorption signal with a predicted absorption value, said predicted absorption value predicted for a time of the current absorption signal, whereby said ratio contains substantially current values;
   means for detecting peak concentration in real time of said flowing substance using said ratio;
   means for detecting the exact time at which said peak concentration exists; and
   means for determining type and concentration of said substance.

2. An absorbance detector according to claim 1, wherein said spectroscopic controller includes means for linearly projecting at least two previous measurements of said first absorbance value to produce said first predicted absorbance value.

3. An absorbance detector according to claim 1, wherein said spectroscopic controller includes means for non-linearly projecting a plurality of previous measurements of said first absorbance value to produce said first predicted absorbance value.

4. An absorbance detector for measuring concentration of a substance, comprising:
   a light source;
   a flow cell having inlets and outlets where said substance flows through;
   a spectroscope between said light source and said flow cell;
   a spectroscopic controller for controlling said spectroscope to pass alternately first and second wavelengths from said light source at first and second times therethrough and into said flow cell;
   means for detecting said first and second wavelengths passing through said flow cell;
   first means, responsive to said means for detecting, for determining a first absorption signal at said first wavelength;
   second means, responsive to said means for detecting, for determining a second absorption signal at said second wavelength; and
   a chromatographic ratio calculator for determining a signal that represents a ratio between said first absorption signal and said second absorption signal, wherein said chromatographic ratio calculator includes:
   means for projecting a plurality of signals representing a plurality of past values of said first absorption signal to predict a value of said first absorption signal at a time of measurement of said second absorption signal, said chromatographic ratio calculator employing a current absorption signal with a predicted absorption value, said predicted absorption value predicted for a time of the current absorption signal, whereby said ratio contains substantially current values;
   means for detecting peak concentration in real time of said substance using said ratio;
   means for detecting the exact time at which said peak concentration exists; and
   means for determining type and concentration of said substance.

5. Apparatus according to claim 4, wherein said spectroscopic controller for controlling is further effective for synchronizing operation of said first and second means.

6. Apparatus according to claim 4, wherein said spectroscopic controller for controlling is further effective for synchronizing operation of said chromatographic ratio calculator means for ratioing.

* * * * *